United States Patent [19]

Schacht et al.

[11] Patent Number: 5,738,864
[45] Date of Patent: Apr. 14, 1998

[54] DRUG DELIVERY AGENTS INCORPORATING MITOMYCIN

[75] Inventors: Etienne Honore Schacht, Staden, Belgium; Ruth Duncan, London, United Kingdom; Paolo Ferruti, Milan, Italy

[73] Assignee: European Community, Luxemburg, Germany

[21] Appl. No.: 602,733

[22] PCT Filed: Aug. 17, 1994

[86] PCT No.: PCT/IB94/00259

§ 371 Date: Feb. 20, 1996

§ 102(e) Date: Feb. 20, 1996

[87] PCT Pub. No.: WO95/05200

PCT Pub. Date: Feb. 23, 1995

[30] Foreign Application Priority Data

Aug. 18, 1993 [GB] United Kingdom ............. 9317213

[51] Int. Cl.⁶ .............. A61K 9/32; A61K 47/30; A01N 43/38; A01N 25/08

[52] U.S. Cl. .............. 424/426; 424/78.17; 424/488; 514/410; 514/772.1; 514/785

[58] Field of Search .............. 424/426, 78.17, 424/488; 514/410, 772.1, 785

[56] References Cited

PUBLICATIONS

DeMarre et al. Apr. 1, 1994 J controlled release 31 pp. 89–87.

DeMarre et al. Aug. 1, 1994 J controlled release 32 pp. 129–137.

*Primary Examiner*—Marian C. Knode
*Assistant Examiner*—Mary K. Zeman
*Attorney, Agent, or Firm*—Cushman Darby & Cushman IP Group of Pillsbury Madison & Sutro LLP

[57] ABSTRACT

A conjugate of a carrier polymer and aziridine ring containing mitomycin (MMC) drug molecules is prepared by coupling the MMC molecules via their aziridine imino groups to spacer groups that terminate in protected amino groups, deprotecting said amino groups, recovering and purifying the spacer-MMC derivatives, and then coupling these derivatives via said deprotected amino groups to the carrier polymer. Alternatively, the MMC may first be treated with an activating agent, e.g. carbodiimidazole, to form an activated MMC derivative which is then coupled directly to spacer groups linked to the carrier polymer.

26 Claims, No Drawings

DRUG DELIVERY AGENTS INCORPORATING MITOMYCIN

This application is a 371 of PCT/IB94/00259 filed Aug. 17, 1994.

FIELD OF THE INVENTION

The present invention relates to the field of pharmaceutical products for use in chemotherapy, especially cancer chemotherapy. More particularly, the invention is concerned with providing drug-delivery agents in the form of polymer/drug conjugates comprising aziridine ring containing mitomycin compounds, such as the anti-neoplastic drug mitomycin-C (abbreviated MMC), covalently coupled through linking spacer groups to macromolecules that can serve as relatively inert polymeric drug carriers in biological systems.

BACKGROUND

Mitomycin-C, which has the structure shown below, has been known for some time as a promising antitumour drug, being a cytotoxic agent that appears to be effective against a number of human cancers. There is currently particular interest in developing methods of using it for the treatment of colorectal and other cancers. Up to now, however, its clinical application has been severely limited due to unacceptable levels of general toxicity and side effects when administered as the free drug. In consequence, it has generally been used clinically only in low doses and in combination with other drugs.

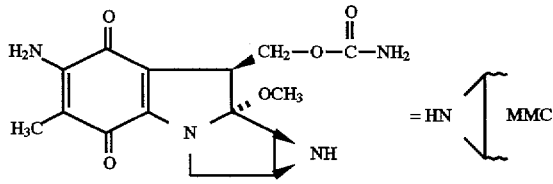

In the hope of reducing these disadvantages of mitomycin-C for clinical use and of improving targeting of the drug to the particular tissues where its effect is required, some attempts have already been made by Japanese research groups to develop macromolecular drug carrier systems in which conjugate compounds are formed by attaching or coupling molecules of the mitomycin-C through covalent linkages to biologically compatible macromolecules or polymers so as to provide drug delivery agents that, after administration, may transport the drug to the tissues concerned, preferably in a selective manner. See, for example, Y. Takakura et al, *Pharmaceutical Research*, 7, No. (1990); C. F. Roos et al, *International Journal of Pharmaceutics*, 22 (1984); and Y. Kaneo et al, *"Preparation and Properties of a Mitomycin-C albumin Conjugate"* published 1990 by the Department of Pharmacy & Pharmaceutical Sciences, Fukuyama University, under the auspices of the Pharmaceutical Society of Japan.

Many proposals are already well documented in the literature for the general design and use of drug delivery systems in which macromolecules, in the form of natural, synthetic or semi-synthetic polymers, are used as carriers for bioactive drug molecules which may be coupled thereto to form a polymer/drug conjugate through spacer groups and biodegradable covalent linkages adapted to permit a controlled or sustained release of the drug within the body of the recipient, such release in some instances occurring actually within particular tissue cells that are able to take up and internalise The polymer/drug conjugate, usually by the process of pinocytosis. At least with soluble biologically inert macromolecular polymer carriers capable of becoming distributed or circulating within The body, apart from the fact that such carriers may naturally tend to accumulate selectively in certain tissues such as tumour tissues for example, there can also be a possibility of attaching or coupling, to the polymer carrier, residues or molecular entities, termed targeting moieties or determinants, that are capable of recognising and interacting with specific sites or cell surface receptors whereby the polymer drug carrier may be more specifically "targeted" to those tissues or cells where the drug is required to act. Thus, such targeting moieties or determinants, which can include molecular entities such as hormones, antibodies or antibody fragments, and other proteins, can permit site-specific drug delivery. Once at the target location, drug release may then take place by biodegradation or cleavage of The bonds linking or coupling the bioactive drug molecules to the polymer carriers, e.g. by hydrolytic cleavage promoted by intracellular enzyme systems, especially lysosomal enzyme systems, following pinocytic uptake of The carrier/drug conjugate.

However, although macromolecular drug carrier systems in theory afford a possibility of restricting the distribution and of controlling the release of drugs within the body, thereby improving their therapeutic index, for successful practical applications it is generally essential to be able reliably to prepare in a reproducible manner well-defined or well-characterised macromolecular polymer conjugates containing an adequate payload of drug molecules with suitable drug/polymer linkages capable of undergoing controlled biodegradation in the desired target areas. Especially for satisfying the latter requirement it is generally necessary to include intermediate linking units or spacers, containing for example a number of degradable bonds such as hydrolysable peptide bonds, between the drug molecules and the main polymer chain. The size and nature of such linking units or spacers can be very important for obtaining satisfactory drug release characteristics.

In the previously reported work by the above-mentioned Japanese research groups to develop macromolecular carrier conjugates of mitomycin-C, various polymers have been used as drug carriers, including dextran, polyamino acids such as poly-L-glutamic acid, poly-L-aspartic acid and polylysine, and also bovine serum albumin. In this previous work, however, the general strategy adopted for endeavouring to prepare the desired conjugates has involved first modifying the polymers to attach spacer groups providing reactive side chains, especially side chains containing a terminal carboxylic acid, to which unmodified MMC molecules are directly coupled in a final stage of the synthetic procedure. Unfortunately, the end products obtained using these methods have been found to possess poorly characterised chemical structures of uncertain or highly variable composition, complicated by the occurrence of various unwanted side reactions, and the results of this work have been found difficult reliably to reproduce. In general, the characterisation of polymer derivatives prepared by a sequence of reactions starting from the parent polymer is not straightforward since most reactions on polymeric side-chain groups are not quantitative; hence this method of synthesis is not ideal for pharmaceutical application. Thus, the practical preparation or synthesis in a reproducible manner of satisfactory well defined MMC/polymer conjugates suitable for clinical use still presents a problem.

An object of the present invention is accordingly to provide an improved process for synthesising macromolecular polymer carrier conjugates of mitomycin compounds such as mitomycin-C which can give well-characterised chemical structures better suited for clinical use as drug delivery agents.

SUMMARY OF THE INVENTION

According to one aspect of the present invention, a process for synthesising a polymer/drug conjugate composed of polymer carrier in the form of a biologically inert macromolecule covalently coupled through linking spacer units to molecules of mitomycin-C or other therapeutically active mitomycin compound containing an >NH group in the aziridine ring thereof is characterised by a first step of (a) modifying said mitomycin compound to produce a reactive derivative thereof in which the mitomycin aziridine ring >NH group is either converted by an activating agent into an activated group capable of reacting with aliphatic amines or is covalently coupled to a side chain which is suitable for providing a said spacer unit and which terminates in a primary amine reactive amino group —$NH_2$; and then, in a subsequent separate stage (b) a second step of reacting said reactive mitomycin derivative with said polymer carrier which is presented in a form that contains at least one reactive group, thereby to establish a coupling through a covalent linkage between said polymer carrier reactive group and said reactive mitomycin derivative, either via a said activated mitomycin aziridine ring >NH group or via a said primary amine reactive amino terminal group of a said side chain of the mitomycin compound, and thereby producing said polymer/drug conjugate.

In this process in accordance with the invention, where the reactive mitomycin derivative includes said spacer unit side chain, this derivative, or a preceding intermediate derivative of the mitomycin compound in which the terminal amino group of the side chain is temporarily protected by a removable protective group, will generally be isolated, purified and well characterised before the final coupling reaction with the polymer.

In many preferred embodiments the polymer carrier will contain amino reactive side groups and will be reacted with the reactive mitomycin derivative that includes the side chain which terminates in a reactive amino group —$NH_2$, whereby coupling takes place and a covalent linkage is established between the polymer carrier and the mitomycin molecule so that the said side chain does in fact provide a said linking unit or spacer. In these preferred embodiments, it has been found that the primary amine terminal amino group of the side chain in the reactive mitomycin derivative is generally much more reactive than the aziridine secondary amine imino group of the unmodified mitomycin molecule. This allows better coupling to be achieved with the reactive polymer, as compared with a direct coupling of an unmodified mitomycin molecule, and the conjugate obtained can be well characterised and will generally be structurally reproducible. The enhanced coupling efficiency, and the possibility of an intermediate isolation and purification step, is also important in that it leads to a minimum amount of unbound mitomycin or other impurity being present in the final product.

The covalent bonding between the polymer carrier and the mitomycin molecule, especially that between the mitomycin molecule and the side chain spacer, will generally comprise biodegradable bonds, susceptible for example to enzymatic or hydrolytic cleavage, thereby enabling active mitomycin drug molecules to be released at their target location within the body during the course of therapeutic treatment.

Although the present invention is applicable generally to aziridine ring containing mitomycin compounds, all of which are intended to be covered by the abbreviation "MMC", it is at present particularly relevant in relation to mitomycin-C which is the mitomycin compound that has been the subject of especial study. Accordingly, the invention will hereinafter be further described with specific reference to mitomycin-C, but it will be understood that in general, unless otherwise stated, the description is equally applicable to other mitomycin compounds that may also be bioactive and the scope of the invention as specified in the claims is not to be regarded as being necessarily limited to mitomycin-C.

Preferably, in preparing the reactive mitomycin derivative that includes an amino terminated side chain for providing a spacer group or unit, the side chain is coupled by way of a urethane (—O—CO—) bond, an amide (—CO—) bond, or a urea (—NH—CO—) bond with the aziridine >NH group of the MMC molecule. Thus, such MMC derivatives formed in carrying out the invention may generally be depicted by one of the following structures:

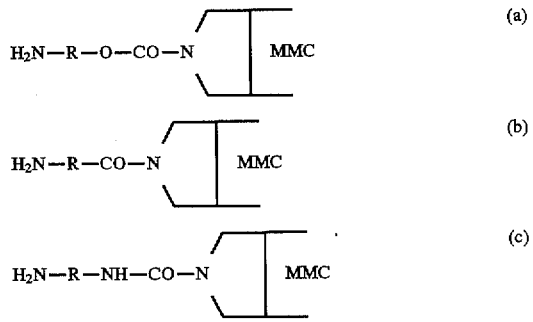

These derivatives, at least those of structures (a) and (b), may conveniently be prepared using hydroxyamines, $H_2N$—R—OH, or amino acids, $H_2N$—R—COOH, as starting materials. These compounds may be coupled to the MMC molecules after first activating the hydroxyl or carboxyl group to convert it into a more reactive form suitable for coupling to the MMC aziridine >NH group. An important feature of the present invention, however, in relation to the preparation of these particular derivatives from such starting materials is the fact that before activating the hydroxyl or carboxyl group thereof and coupling of the side chain or spacer to the mitomycin-C, the terminal amino group is protected with a suitable protective group that can subsequently be removed without damage to or degradation of the MMC molecule. Since MMC is sensitive to acids and reducing agents, amino protective groups that require acid treatment or hydrogenolysis for removal are not suitable. A preferred amino protective group is fluorenyl methyloxycarbonyl (Fmoc) which can be removed by treatment with a base, e.g. a trialkyl or tertiary amine such as triethylamine, under mild conditions, i.e. at about or below room temperature. Other suitable protective groups can be used, however, such as the allyloxycarbonyl group $CH_2$=CH—$CH_2$—O—CO— which can also be removed under mild conditions by treatment with tetrakis(triphenylphosphine)palladium(O) using dimedone (5,5-dimethyl-1,3-cyclohexane dione) as an allyl scavenger.

Thus, typical reaction schemes for preparing the required reactive MMC derivative, where Z represents an activated group, may be depicted as follows:

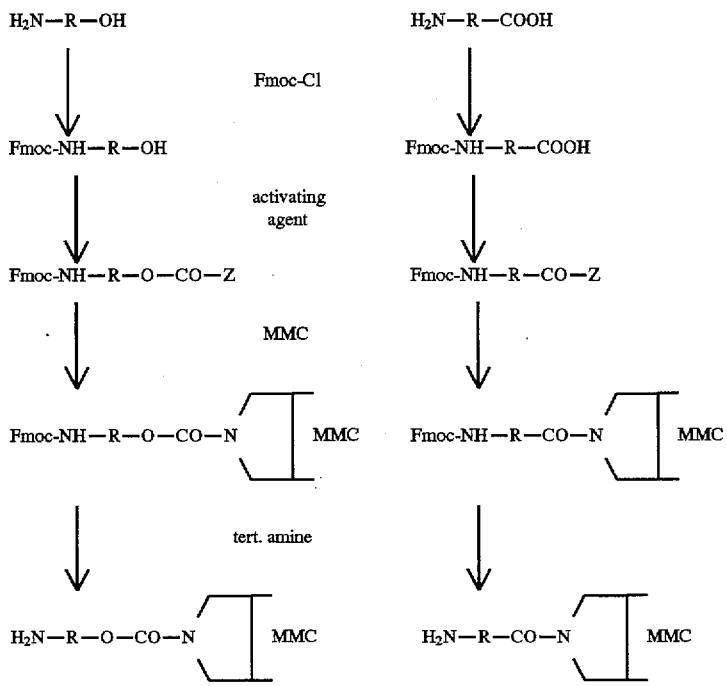

For the activation step, various activation agents may be used which produce derivatives that react well with amino groups of aliphatic amines. A typical example is carbonyl di-imidazole (CDI), in which case Z will be a reactive imidazolide group. CDI will often be a preferred activating agent, but, alternatively, hydroxyl groups can be activated by reaction with chloroformates such as 4-nitrophenyl chloroformate, pentafluorophenyl chloroformate, succinimidyl chloroformate, etc. For the activation of the COOH groups, other methods well known in peptide chemistry can be used to convert the acid to a reactive derivative. Such methods include for instance the formation of reactive esters (e.g. 4-nitrophenyl ester, succinimide ester, etc.) or mixed anhydrides (e.g. isobutyloxycarbonyl, pivaloyl . . . ).

For preparing derivatives of structure (c) which contain the —NH—CO— urea linkage, the above procedure is preferably modified by first treating the MMC with CDI or other activating agent to provide the MMC molecule with a reactive imidazolide group, or other amino reactive group, linked to the aziridine NH group. This is then reacted with an excess of a diamine compound $H_2N—R—NH_2$ to form the structure (c). In this case, no amino protective group is needed.

The technique of treating the mitomycin with an activating agent such as CDI so as to provide an amino reactive group linked to the aziridine >NH is also useful in other embodiments of the invention wherein such activated MMC molecules are coupled direct to amino terminated side chains or groups of the polymer carrier.

The invention also includes mitomycin derivatives such as are herein disclosed having a side chain terminated with an amino or protected amino group, of general formula

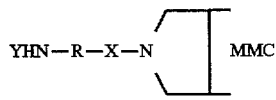

where X is a linkage —CO—, —O—CO— or —NH—CO— and Y is H or an amino protective group.

A wide choice is available for selection of the main group R of the side chain or spacer unit, including aliphatic and aromatic moieties and amino acid or oligopeptide sequences. For example, where Y is hydrogen, the portion $H_2N—R—$ may include any of the following:

$H_2N—(CH_2)_n—$ $H_2N—(CH_2)_n—CO—NH—$ $H_2N—Ph—CO—NH—(CH_2)_n—$ where n is an integer in the range of 1 to 20, or is $H_2N—Ph—$, or is an amino acid or oligopeptide sequence.

In many cases, peptide spacers will be preferred for the linkages between the polymer carrier and the mitomycin molecules, but the number of peptide units and the amino acid composition thereof in the spacer groups may have an important influence on the stability and release characteristics of the drug molecules in vivo, as already indicated. This has been shown most clearly by some experiments carried out on polymer/drug conjugates composed of mitomycin-C molecules coupled through various tripeptide or tetrapeptide spacers to poly[N-(2-hydroxyethyl)-L-glutamine] (PHEG) as the polymeric carrier. These conjugates were prepared in accordance with the invention by first coupling the peptide spacer groups with MMC to provide reactive derivatives of the latter. These derivatives, which could readily be purified and characterised, were then coupled onto the PHEG polymeric carrier, and in order to examine the influence of spacer composition on MMC release rate, the macromolecular polymer/MMC conjugates were incubated under controlled conditions in buffer, bovine serum and in the presence of lysosomal enzymes (tritosomes). It was found in general that conjugates with a hydrophobic terminal amino acid in the spacer group are hydrolyrically more stable than those with a hydrophilic terminal amino acid such as glycine. In addition, it has been found that tetrapeptide spacers, especially spacers with amino acid sequences gly-phe-leu-gly, gly-phe-ala-leu or ala-leu-ala-leu, can provide a better substrate for lysosomal enzymes than tripeptide spacers and can be very rapidly degraded by lysosomal proteases to release the free drug.

The polymer carrier chosen will generally be a non-toxic polymer containing functional hydroxyl or carboxyl side groups and may be a natural polymer, a synthetic polymer or a semi-synthetic polymer. In some cases it may be possible to couple carboxyl groups of the polymer directly to the amino-terminated reactive MMC derivative, e.g. in the presence of a suitable catalyst such as a carbodiimide. Usually, however, in preferred embodiments of the invention the polymer will first be converted into a more reactive derivative by activating the hydroxyl or carboxyl functional groups to convert them into a form that reacts readily with primary aliphatic amine amino groups. This may be accomplished, as already indicated in relation to the activation step used in preparing the reactive MMC derivatives, by using activating agents such as carbonyl diimidazole (CDI) to form a reactive imidazolide group or p-nitrophenyl chloroformate to form a reactive p-nitrophenol group, or by using one of various other known methods commonly used in peptide chemistry.

The polymer carriers may be either biostable or biodegradable. Suitable hydroxyl containing polymers include polysaccharides such as dextran and pullulan for example, poly[N-hydroxyalkyl acrylamide] and poly[N-hydroxyalkyl methacrylamide], poly(N-hydroxyalkyl-glutamine)s, e.g. poly[N-(2-hydroxyethyl)-L-glutamine] (PHEG), poly[N-hydroxyethyl)-aspartamide], poly(amidoamines)s with hydroxyl terminated side chains or side groups, and poly (phosphazene) derivatives, e.g. poly[N-(2hydroxyethyl) phosphazene]. Suitable carboxyl containing polymers include poly(amidoamine) derivatives with —COOH side groups, poly(glutamic acid), succinylated polylysine, copolymers of vinyl pyrrolidone and maleic anhydride, succinylated hydroxyl containing polymers, etc.

A typical conjugate based on PHEG as the polymer carrier may be represented as shown below, where the ratio x:y may vary between 0 and 3 for example.

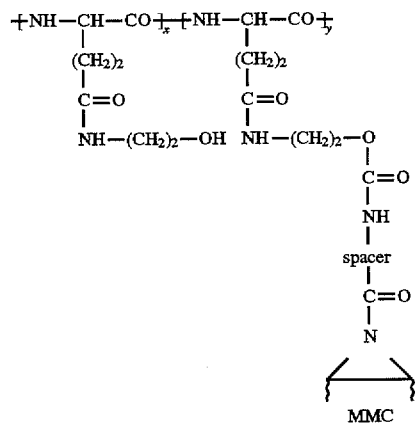

The polymers may have a wide variety of molecular weights, ranging on average for example from several hundred to tens or hundreds of thousands of daltons. For use in biological systems, however, it will usually be preferred that they be water soluble polymers.

The number of amino reactive groups formed along the polymer chain will generally be controllable by the relative amount or quantity of activating reagent used and by the reaction conditions. For example, in the case of dextran, using p-nitrophenyl chloroformate in DMSO (dimethylsulphoxide)/pyridine at 5° C. to form the p-nitrophenyl carbonate —O—CO—ONp (ONp=p-nitrophenoxy) or the cyclic carbonate derivative which both react smoothly with primary amines (aminolysis) to produce a corresponding urethane derivative, by varying the amount of chloroformate added and the reaction conditions any activation percentage between 0% and 30% of the anhydro glucoside units in the dextran chain can be achieved.

It will be appreciated, however, that not all the activated or reactive functional groups of the polymer need necessarily be utilised in coupling to the amino-terminated MMC derivative and some may be utilised for attaching one or more targeting moieties or determinants capable of recognising and interacting with specific sites or cell surface receptors, as previously referred to. Attachment of such targeting moieties or determinants may be carried out either before or after coupling to the MMC derivative, the extent or degree of coupling of these different molecular entities again being controllable by adjusting the relative amounts of reagents used and reaction conditions.

Especially useful for incorporating in these well-characterised polymer/MMC conjugates are targeting moieties or determinants such as antibodies or antibody binding fragments or oligopeptides that are effective in recognising specific cell membrane receptors of tumour cells, thus enabling specific tumour-targeted MMC conjugates to be synthesised.

Among the possible synthetic polymers that may be used as MMC carriers, poly(amidoamine)s in which tertiary amino and amido groups are regularly arranged along the polymer main chain (see for example Ferruti et al, "Advances in Polymer Science" (1984), 58, 57) can be especially useful. Such poly(amidoamine) polymers, which may include block copolymers and which may have advantageous pH-dependent conformational characteristics, can generally be prepared in a well-characterised form with pendant side chains terminating in —OH or —COOH groups that can be activated by the methods herein described (e.g. treatment with carbonyl diimidazole). These can then be coupled directly to a reactive MMC derivative, prepared as herein described, to provide satisfactory conjugates.

If, in preparing such poly(amidoamine)/MMC conjugates, the reactive mitomycin derivative is produced by treating MMC directly with an activating agent such as carbonyl diimidiazole (CDI), if desired a spacer group or unit provided by a diemine compound may be incorporated in a side chain of the polymer to modify the latter (after suitable activation of a hydroxyl or carboxyl group thereof), instead of being included as a side chain of the MMC molecule. For example, with a polyamidoamine that includes a repeating unit

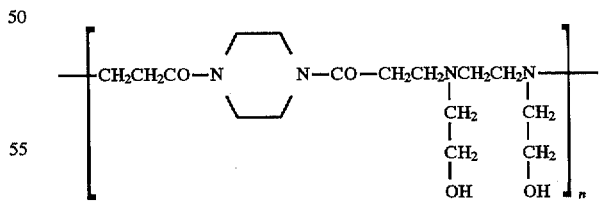

this may first be modified by treatment with CDI and excess of a diemine compound, e.g. ethylene diemine or piperazine, so that the pendant side chains terminate in an amine group that, being a reactive group, can be coupled directly to an activated derivative of mitomycin which is also produced by treatment with CDI as an activating agent. This general reaction scheme, in relation to one of the —OH terminated pendant side chains of the poly(amidoamine) may be illustrated diagrammatically as follows:

a) Preparing modified polyamidoamine (PAA) by activating side chain hydroxyl groups with CDI and reacting with excess diemine

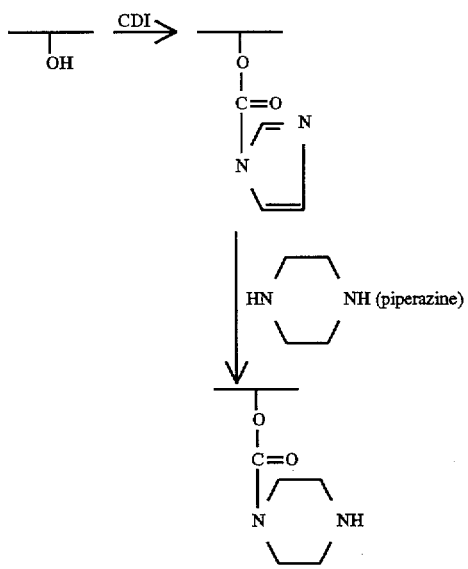

b) Preparation of an activated derivative of MMC by reaction with CDI:

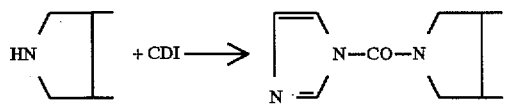

c) Reaction of the modified PAA carrier with the activated derivative of MMC:

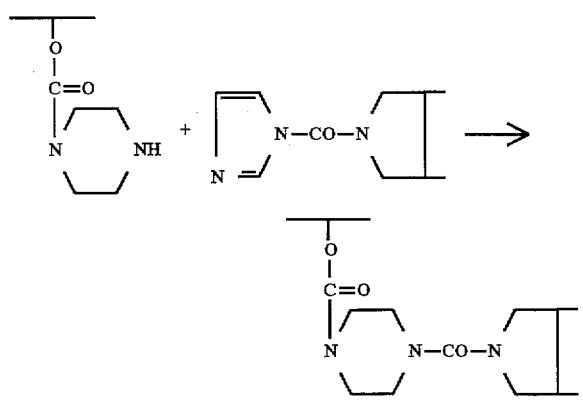

The invention also includes pharmaceutical formulations or compositions comprising polymer/MMC conjugate compounds produced as herein disclosed, especially conjugate compounds in which the carrier polymer contains both mitomycin-C drug molecules and a "targeting" moiety, made up for administration in any suitable manner, for example parenterally (including intravenously, intramuscularly and subcutaneously) or orally. Such formulations, containing for example therapeutically effective amounts or dosages of the polymer/MMC conjugate together possibly with at least one other ingredient providing a compatible pharmaceutically acceptable additive, diluent or excipient, may be prepared by any of he methods well known in the art of pharmacy.

The invention also includes all novel and inventive features and aspects herein disclosed, either explicitly or implicitly and either singly or in combination with one another, and the scope of the invention is not to be construed as being limited by the illustrative examples or by the terms and expressions used herein merely in a descriptive or explanatory sense.

DETAILED DESCRIPTION

By way of further background explanation and description of the invention, some more detailed examples are hereinafter presented relating to the preparation of typical polymer/MMC conjugates in accordance with the invention.

EXAMPLE 1

Synthesis of Dextran-MMC Conjugate by First Route a) Preparation of a 6-N-[fluorenylmethyloxycarbonyl] aminohexanoyl derivative of mitomycin-C (Compound I)

A 6-N-[fluorenylmethyloxycarbonyl]amino hexanoyl derivative of mitomycin-C has been prepared by reacting an activated derivative of N-protected 6-aminohexanoic acid with mitomycin-C. Of the several possible activated derivatives of the carboxylic acid which could be used, including 4-nitrophenyl-ester, pentafluorophenylester etc., in this example an imidazolide derivative, prepared by reacting the said acid with carbonyl diimidazole, was used. The reaction scheme was as follows:

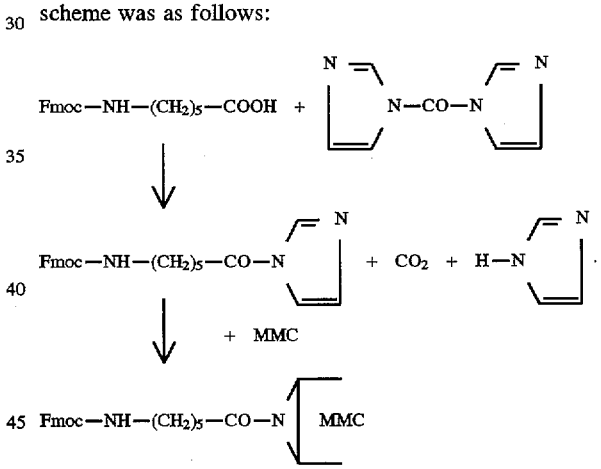

Experimental Part

To a solution of 0.2 g of Fmoc-aminocaproic acid in 10 ml of dry tetrahydrofuran (THF) was added 0.11 g carbonyl diimidazole. The solution was stirred for 1 hour at room temperature. An 0.2 ml aliquot was withdrawn and analysed by NMR. Quantitative conversion was demonstrated. To the reaction medium was then added a solution of 189 mg MMC in 10 ml dry THF. The solution was stirred in the dark and at room temperature for 2 weeks. The solution was finally concentrated and the desired reaction product in the reaction mixture was separated by preparative adsorption chromatography on silica (eluent $CHCl_3$/MeOH: 9/1).

The yield of the desired MMC derivative was 45% based on MMC added. The structure was confirmed by $^1H$ NMR.

b) Preparation of 4-nitrophenylchloroformate activated dextran (Compound II)

As an example the synthesis is described of a dextran derivative having 5 molar percentage of anhydroglucose units substituted with a reactive carbonate ester:

Experimental Part

To a solution of 200 mg dextran in 20 ml DMSO/pyridine (1/1, v/v) was added 20 mg 4-nitrophenylchloroformate and 5 mg 4-N,N-dimethylaminopyridine. The mixture was stirred for 4 hours at 0° C. and then precipitated in 100 ml of an ethanol/ether (1/1) mixture. The precipitate was collected and repeatedly washed with dry ether.

Titrametric and UV spectroscopic analysis indicated the derivative to contain 5 mol percent reactive carbonate esters. By adjusting the amount of chloroformate added, reactive derivatives with a degree of substitution varying between 1 and 30 percent can be prepared.

c) Deprotection of the N-Fmoc-6-aminohexanoyl MMC derivative and coupling with chloroformate activated dextran to produce polymer conjugate To a solution of 20 mg of the N-Fmoc-6-aminohexanoyl mitomycin-C derivative (Compound I) dissolved in 3 ml of dry dimethylsulfoxide was added 0.5 ml dry triethylamine. The mixture was stirred for 1 hour at room temperature and then added to a DMSO/pyridine solution of the 4-nitrophenyl chloroformate activated dextran (Compound II). This mixture was stirred overnight at room temperature. Then 0.5 ml of aminoethanol was added. After 2 hours stirring the reaction mixture was precipitated in a 1:1 ether/ethanol mixture. The precipitate was collected and washed repeatedly with dry ether.

The MMC content in the polymer conjugate was analysed by UV spectroscopy. The degree of substitution (DS) was found to be 3 mol percent.

d) Analogous Derivatives

In a similar manner MMC derivatives having other $\alpha,\Omega$ amino carboxylic acids substituted on the aziridine ring N-atom can be prepared as described above.

EXAMPLE 2

Synthesis of Dextran-MMC Conjugate by Second Route a) Preparation of 2-N-(fluorenylmethyloxycarbonyl) aminoethanol To a solution of 0.5 g 2-aminoethanol in 20 ml of 10% $Na_2CO_3$ was added, with stirring and cooling in an icebath, a solution of 1.96 g fluorenylmethyloxycarbonyl chloride in 10 ml dioxane. The mixture was stirred for 2 hours at room temperature. The precipitate formed was removed by filtration, washed with water and finally dried over $P_2O_5$. The structure was confirmed by $^1H$ NMR.

b) Preparation of a 2-N-Fmoc-aminoethyloxycarbonyl derivative of MMC (Compound III)

100 mg of 2-N-Fmoc-aminoethanol, prepared as described above, was dissolved in 15 ml dry THF. 57 mg carbonyl diimidazole was added and the mixture was stirred at room temperature for 2 hours. Then 118 mg MMC dissolved in 10 ml THF was added. Stirring was continued for 2 weeks. The reaction mixture was finally concentrated and the desired reaction product was isolated by preparative absorption chromatography on silica (eluent: $CHCl_3$/MeOH, 9/1). The yield, based on MMC used, was 42%. Structure was confirmed by $^1$NMR.

c) Deprotection of the N-Fmoc-aminoethyloxycarbonyl MMC derivative and coupling with chloroformate activated dextran

Reaction Scheme

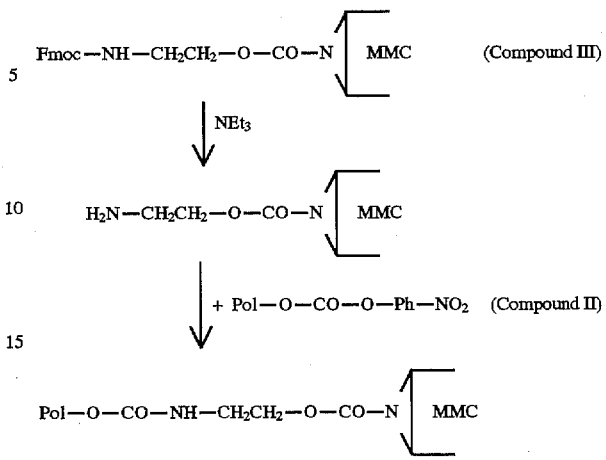

Experimental Part 25 mg of the 2-N-Fmoc-aminoethyloxycarbonyl MMC derivative was dissolved in 5 ml dry DMSO. 0.2 ml triethylamine was added and the mixture was stirred for 2 hours. It was then added to B solution of 200 mg of the 4nitrophenylchloroformate activated dextran (Compound II-DS: 5%) dissolved in 20 ml DMSO/pyridine. Stirring was continued overnight. The polymer was precipitated in an excess of ether/ethanol (1/1), filtered and dried. NMR and LTV analysis indicated the degree of substitution (DS) to be 3 mol percent.

EXAMPLE 3

Synthesis of PHEG-Oligopeptide-MMC Conjugates
Stage 1. Preparation of peptide-MMC derivatives All peptide-MMC derivatives were prepared using the same strategy. As an example is given the synthesis of gly-phe-gly-MMC.

a) Fmoc protection of the peptide 0.2 g of gly-phe-gly (0.0725 mmol) was dissolved in 5 ml of a 10% solution of $Na_2CO_3$ in water/dioxane mixture (vol. ratio 2/1) and cooled in an ice bath. Then 0.182 g of Fmoc-Cl (0.7025 mmol), dissolved in 1 ml dioxane, was added. The reaction mixture was stirred for 2 hours at room temperature and added to 50 ml of water. After extraction with ether (20 ml) the aqueous layer was acidified with concentrated HCl. The white precipitate was extracted with ethylacetate. The combined ethylacetate fractions were dried on magnesium sulphate. After evaporation of the solvent the protected peptide was obtained as a solid (yield 85%). The product was characterized by $^1H$ NMR spectroscopy (360 MHz) in DMSO-d6: $\delta$=2.9 ppm:$H_A$ $CH_2$-phe, $\delta$=3.2 ppm:$H_B$ $CH_2$-phe, $\delta$=3.7 ppm:$CH_2$-gly, $\delta$=3.9 ppm:$CH_2$-gly, $\delta$=4.2 ppm:CH-Fmoc, $\delta$=4.35 ppm:$CH_2$-Fmoc, $\delta$=4.65 ppm CH-phe, $\delta$=7.2 ppm:arom. protons phe, $\delta$=7.3–7.8 ppm:arom. protons Fmoc.

By comparing the integrations of the signals at 7.3–7.8 (aromatic protons of Fmoc) and the signals of the different aminoacids in the peptide e.g. 7.1–7.2 ppm (aromatic protons of phe) complete protection could be confirmed. Typical yield of the reaction: 70–80%.

b) Synthesis of the pentafluorphenyl ester of the Fmoc-peptide 0.18 g of Fmoc-gly-phe-gly (0.355 mmol) and 0.078 g of pentafluorophenol (0.425 mmol) were dissolved in 3 ml dry THF. After cooling to 0° C., 0.073 g of dicyclohexylcarbodimide (DCC) (0.355 mmol) was added. The reaction was stirred for 2 hours at 0° C. and overnight at room temperature. After filtration of dicyclohexylurea (DCU) and concentration of the solution, the reaction product was obtained by precipitation in a 1/1 mixture of ether/hexane.

All other peptides were converted into reactive esters following the same procedure. The reactive esters were characterized by IR spectroscopy (aromatic ester: 1790 cm$^{-1}$) and TLC (eluent:CHCl$_3$/MeOH 9/1). Typical yield of the reaction: 80–90%.

c) Coupling together the MMC and the reactive ester 0.18 g of Fmoc-gly-phe-gly pentafluorophenyl ester (0.267 mmol) and 0.089 g of MMC 9 (0.267 mmol)were dissolved in 5 ml DMF and 0.1 ml of pyridine was added. After 48 hours reaction in the dark at room temperature, the solvent was evaporated under vacuum (temperature not exceeding 30°–40° C.) and the residue was purified by column chromatography on silica (eluent: CHCl$_3$/MeOH 9/1). The selected fraction was dried over MgSO$_4$. After removal of the solvent the Fmoc-gly-phe-gly-MMC derivative was finally obtained as a blue solid.

$^1$H NMR in MeOD-d4:$\delta$=1.7 ppm:CH$_3$-MMC, $\delta$=2.9 ppm:H$_A$-phe, $\delta$=3.1 ppm: H$_{B\text{-}Phe+OCH3}$-MMC, $\delta$=3.4–3.65 ppm: H2,H3',H1 H9- MMC, $\delta$=3.65–3.8 ppm:CH$_2$-gly, $\delta$=3.85–4.1 ppm:CH$_2$:gly+H10- MMC, $\delta$=4.2 ppm:CH-Fmoc, $\delta$=4.35 ppm:CH$_2$-Fmoc, $\delta$=4.45 ppm:H3- MMC, $\delta$=4.65 ppm: CH-phe, $\delta$=4.75 ppm:H10'-MMC, $\delta$=7.15 ppm:arom.protons phe, $\delta$=7.25–7.8 ppm:arom.protons Fmoc.

The same method was applied for the other Fmoc-peptide-MMC derivatives. All derivatives were characterized by $^1$H NMR analysis in MeOD-d4. The integrations of the most important signals of MMC (CH$_3$:1.7 ppm), Fmoc (aromatic protons:7.3–7.8 ppm) and signals from the different aminoacids in the peptide were compared and complete conversion was observed. Typical yield of the reaction: 60–70%.

d) Removal of the Fmoc protecting group 0.05 g of Fmoc-gly-phe-gly-MMC was dissolved in 1 ml DMF, 0.1 ml of triethylamine (TEA) was added. After reaction for 3 hours at room temperature the solvent was evaporated under vacuum (temperature not exceeding 30°–40° C.). The residue was dissolved in 3 ml MeOH and the solution was filtered. The amine containing peptide-MMC conjugate was finally obtained after evaporation of the solvent. After NMR analysis in MeOD-d4 no signals from Fmco could be detected all other signals had the same chemical shift as described above.

Stage 2. Synthesis of PHEG

PHEG can be prepared by aminolysis of poly-gamma-benzyl-L-glutamate (PBLG) with 2-amino-1-ethanol. PBLG was prepared using standard procedure: the N-carboxyanhydride (NCA) of gamma-benzyl-L-glutamate was prepared by the method of Daly. The NCA was polymerized at room temperature in dioxane in the presence of triethylamine as the initiator. After polymerization for 3 days, PBLG was precipitated in excess ether, filtered and dried. Aminolysis of PBLG with 2-hydroxypyridine as a catalyst (20 mol %), was carried out in DMF as a solvent. The reaction mixture was stirred at room temperature for 48 hours. PHEG was precipitated in excess ether, filtered and dialyzed against water for 2 days. After freeze-drying pure PHEG was obtained as a white powder. The molecular weight was determined by gel-permeation chromatography (GPC) with water an eluent (TSK-G3000SW, G2000SW) using dextran standards (MW=88500, 33100 and 10000). The number- and weight-average molecular weights were Mw=16500 and Mn=13000.

Stage 3. 4-nitrophenyl chloroformate activation of PHEG 0.25 g of PHEG (1.45 mmol units) and 16 mg of 4-dimethyl-aminopyridine (0.13 mmol) were dissolved in 6.35 ml of a NMP/pyridine solution (vol. ratio 4/1), 0.176 g of chloroformate (0.87 mmol) was added at 0° C. After 4 hours reaction at 0° C. the reaction mixture was precipitated in an anhydrous ether/ethanol mixture (vol. ratio 2/1). A white precipitate was collected and washed repeatedly with the same mixture. The product was finally dried. The carbonate content was determined by UV analysis carried out after alkaline hydrolysis in NaOH ($\mu^M$=402 mm, $\epsilon_M$=18400 1 mol$^{-1}$cm$^{-1}$).

Stage 4. Preparation of the polymeric-peptide-MMC conjugates 0.2 g of activated PMEG (4 mol %) and 30 mg of gly-phe-gly-MMC (0.05 mmol) were dissolved in a 15 ml NMP/pyridine solution (vol. ratio 4/1). After 48 hours of reaction in the dark the conjugate was separated by precipitation in an anhydrous ether/ethanol mixture (vol. ratio 2/1). The product was washed and dried. Finally the conjugate was purified by preparative GPC (Sephadex G25) with water and freeze-drying.

The degree of MMC substitution in the conjugates was determined by UV analysis in water ($\mu_M$=364 mm, $\epsilon_M$=22000 1 mol$^{-1}$ cm$^{-1}$). The molar and weight percentages of MMC substitution in the different polymeric-peptide-MMC conjugates prepared by the scheme described above are shown in the following table.

| Peptide | mol % | wt % |
| --- | --- | --- |
| gly—phe—gly | 1.7 | 3 |
| gly—phe—leu—gly | 2.2 | 3.9 |
| gly—phe—leu | 2.9 | 5.1 |
| gly—phe—phe | 3.2 | 5.5 |
| gly—gly—phe | 3.4 | 5.9 |
| gly—gly—phe—leu | 3 | 5.2 |
| gly—phe—ala—leu | 3.6 | 6 |
| ala—leu—ala—leu | 2.9 | 5 |

Testing of the PHEG/MMC conjugates prepared as described above confirmed that the oligopeptide spacers were degradable by lysosomal proteases, and also by collagenase IV (a tumour associated enzyme), to release free MMC, this enzymic degradation and controlled release being particularly efficient in acidic solution (e.g. about pH 5.5) for tetrapeptide spacers having a hydrophobic terminal amino acid. Also, it has been shown that these PHEG/MMC conjugates were far less toxic towards bone marrow than MMC itself. In addition, from in vivo tests using BALB/c mice it has been established that these PHEG-MMC conjugates are particularly effective as cytotoxic agents against solid tumours resulting from implanted C26 colorectal carcinoma cells.

EXAMPLE 4

Preparation of MMC-Polyamidoamine Conjugate a) Preparation of polyamidoamine (PAA)

6.0267 g of 1,4-bis(acryloyl)piperazine (0.0310 mol), 1.5328 g of N,N'-bis(2-hydroxyethyl)ethylenediamine (0.0103 mol) and 2.0720 g of 2-methylpiperazine (0.0207 mol) are dissolved in 15 ml of water. The reaction mixture is allowed to stand at 30° C. under nitrogen atmosphere for 24 hours and freeze-dried (yield 9.63 g). At this point 1.54 gq of the freeze-dried product are dissolved in 20 ml of anhydrous (N,N-dimethylformamide (DMF) and 0.6413 g of 1,1'-carbonyldiimidazole (purity: 97%, 0.0038 mol) are added. After the reaction mixture has been stirred for 30 minutes at 25° C., 2.90 g of piperazine (0.0337 mol) are added and allowed to react for 12 hours at 60° C. Afterwards, the solution is poured into diethylether (200 ml); precipitation of the PAA occurs: the supernantant is removed and the PAA is washed with diethylether (100 ml); this operation (washing and supernatant removal) is repeated for further three times. Finally the product is carefully dried under vacuum up to constant weight: 1.61 g.

b) Preparation of MMC-polyamidoamine (MMC-PAA) conjugate

After 0.1069 g of Mitomycin C (MMC) (0.320 mmol) have been dissolved into 1 ml of anhydrous DMF, 0.0572 g of 1,1'-carbonyldiimidazole (purity: 97%; 0.0342 mmol) are added and allowed to react for 2 hours at 25° C. in the dark. Then 0.1844 g of dry PAA (synthesized as described in (a) above) are added, as well as 3 ml of anhydrous DMF. The reaction mixture is maintained at 30° C. under nitrogen atmosphere and in the dark for 90 hours. Then it is diluted up to 20 ml with methanol/DMF 1:1 mixture and poured into ethyl acetate (200 ml) with stirring. Stirring is carted on for further 15 minutes, supernatant is removed, MMC-PAA conjugate is dissolved into 10 ml of methanol/DMF 1:1 mixture and precipitated into ethyl acetate (100 ml) under stirring, which is carried on for further 15 minutes. This operation (removal of supernatant, dissolution, precipitation and stirring) is repeated for a further three times. Finally the conjugate is washed with ethyl acetate (100 ml), the supernatant is removed and the product dried under vacuum up to constant weight: 0.1184 g The MMC loading in the MMC-PAA adduct or conjugate (about 18% by weight) was evaluated by means of a U.V. calibration curve based on MMC absorbance at 362 nm. No free MMC could be detected by usual analytical techniques (H.P.L.C., G.P.C., T.L.C.)

We claim:

1. A process for synthesizing a polymer/drug conjugate comprising a polymer carrier covalently coupled through linking spacer units to molecules of mitomycin-C or another therapeutically active mitomycin compound containing an >NH group in the aziridine ring thereof, said process comprising a first step of:

(a) modifying said mitomycin-C or mitomycin compound to produce a reactive derivative thereof, either by
      (i) reacting said mitomycin-C or mitomycin compound with an activating agent so as to convert the mitomycin aziridine ring >NH group into an activated group which reacts with aliphatic amines, or by
      (ii) coupling the mitomycin aziridine ring >NH group through a covalent bond to a side chain which provides said spacer unit and which terminates in a primary amine reactive amino group —NH$_2$;
   and then, in a subsequent separate stage, (b) a second step of reacting said reactive mitomycin derivative with said polymer carrier which is presented in a form that contains at least one reactive group, thereby to establish a coupling through a covalent linkage between said polymer carrier reactive group and said reactive mitomycin derivative, either via a said activated mitomycin aziridine ring >NH group or via a said primary amine reactive amino terminal group of a said side chain of the mitomycin-C or mitomycin compound, and thereby producing said polymer/drug conjugate.

2. The process as claimed in claim 1 wherein the mitomycin aziridine ring >NH group in the polymer/drug conjugate is coupled to its associated said spacer unit by way of a urethane bond, an amide bond or a urea bond.

3. The process as claimed in claim 2 wherein the reactive derivative of the mitomycin-C or mitomycin compound has a structure selected from the group consisting of:

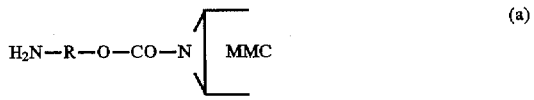

and

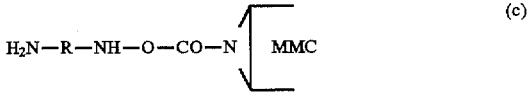

wherein R comprises an aliphatic or aromatic moiety that provides said spacer unit.

4. The process as claimed in claim 3 wherein the structure of the reactive derivative of the mitomycin-C mitomycin compound is selected from the group consisting of:

and

and is prepared by treating either a hydroxyamine H$_2$N—R—OH or a terminally protected amino acid H$_2$N—R—COOH with an activating agent which converts the hydroxyl or carboxyl group thereof into an activated form which reacts with the aziridine imino group of the mitomycin-C mitomycin compound, then reacting the amino-protected activated hydroxyamine or amino acid with said mitomycin-C mitomycin compound to produce an intermediate derivative in which said amino-protected hydroxyamine or amino acid is covalently coupled to the mitomycin via said activated hydroxyl or carboxyl group, followed by isolating and purifying said intermediate derivative and then treating said intermediate derivative to remove the amino protective group (Y) and form the reactive mitomycin derivative ready for step (b) of claim 1.

5. The process as claimed in claim 1, wherein the reactive derivative of the mitomycin-C or compound is prepared by one of the following reaction schemes, where R is an aliphatic or aromatic moiety that provides a said linking spacer unit, Y is an amino protective group and Z is an activated group

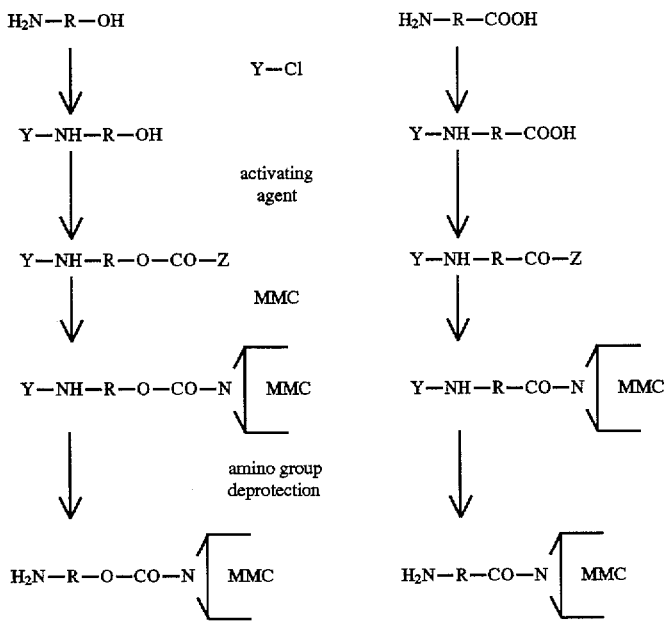

6. The process as claimed in claim 4 or 5 wherein the amino protective group (Y) is fluorenyl methyloxycarbony (Fmoc) or an allyloxycarbonyl group $CH_2\!=\!CH\!-\!CH_2\!-\!O\!-\!CO\!-\!$.

7. The process as claimed in claim 4, wherein
(a) the activating agent used in preparing the reactive mitomycin derivative is carbonyl diimidazole (CDI) or, alternatively,
(b) in the case of preparing the derivative from hydroxyamine, activation of the —OH group is carried out by treatment with a chloroformate or,
(c) in the case of preparing the derivative from an amino carboxylic acid, activation of the carboxyl group is carried out by forming a reactive ester or mixed anhydride.

8. The process as claimed in claim 3 wherein the reactive derivative of the mitomycin-C or compound has the structure (c) of claim 3 and is prepared by treating the mitomycin-C or mitomycin compound with an activating agent to provide an amino reactive group linked to the aziridine ring >NH group, and then reacting this product with an excess of a diamine compound $H_2N\!-\!R\!-\!NH_2$.

9. The process as claimed in claim 3 wherein group $H_2N\!-\!R\!-\!$ is selected from the group consisting of:
$H_2N\!-\!(CH_2)_n\!-\!$,
$H_2N\!-\!(CH2)_n\!-\!CO\!-\!NH\!-\!$, and
$H_2N\!-\!Ph\!-\!CO\!-\!NH\!-\!(CH_2)_n\!-\!$,
where n is an integer in the range of 1 to 20
or is
$H_2N\!-\!Ph\!-\!$
is an amino acid or oligopeptide.

10. The process as claimed in claim 3 in which R is a tripeptide or tetrapeptide.

11. The process as claimed in claim 10 wherein R is a tetrapeptide selected from gly-phe-leu-gly, gly-phe-ala-leu and ala-leu-ala-leu.

12. The process as claimed in claim 10 wherein R comprises a hydrophobic terminal amino acid.

13. The process as claimed in claim 1 in which the polymer carrier is provided by a non-toxic polymer containing functional hydroxyl or carboxyl groups that are activated by treatment with an activating agent selected from the group consisting of carbonyl diimidazole and p-nitrophenyl chloroformate.

14. The process as claimed in claim 13 wherein the polymer carrier is a hydroxyl containing polymer selected from a polysaccharide, a poly(N-hydroxyalkylglutamine), a poly(amidoamines) having hydroxyl side groups, and a poly(phosphazene) derivative.

15. The process as claimed in claim 13 wherein the polymer carrier is a carboxyl containing polymer selected from a poly(amidoamine) derivative having a —COOH side group, poly(glutamic acid), succinylated polylysine, a copolymer of vinyl pyrrolidone and maleic anhydride, and a succinylated hydroxyl containing polymer.

16. A process for synthesising a polymer/drug conjugate incorporating mitomycin-C or another mitomycin compound having anticancer activity containing an >NH group in the aziridine ring, said process comprising the steps of:
(a) preparing a derivative of a hydroxyamine $H_2N\!-\!R\!-\!OH$ or an aminoacid $H_2N\!-\!R\!-\!COOH$ wherein the terminal amino group is protected,
(b) treating said derivative of step
(a) with an activating agent to produce a derivative with hydroxyl or carboxyl group,
(c) reacting the derivative of step (b with the mitomycin-C or mitomycin compound whereby the mitomycin aziridine ring >NH group is covalently coupled to said activated hydroxyl or carboxyl group to provide a side chain, to produce a drug/spacer conjugate
(d) isolating and purifying the conjugate of step (c),
(e) treating the conjugate of step (d) to remove the amino protective group to produce a mitomycin derivative,
(f) reacting the mitomycin derivative produced in step (e) with a polymer carrier containing at least one amino reactive group that reacts to form a covalent linkage with said mitomycin derivative via the deprotected amino terminal group of said side chain, said side chain then forming a spacer unit between the polymer and the mitomycin compound, to produce a polymer/drug conjugate, and (g) recovering the polymer/drug conjugate of step (f).

17. A process for synthesising a polymer/drug conjugate incorporating mitomycin-C or another mitomycin compound having anticancer activity containing an >NH group in the aziridine ring, said process comprising the steps of:

(a) treating the mitomycin-C or mitomycin compound with an activating agent to activate the mitomycin aziridine ring >NH, (b) reacting the activated mitomycin-C or mitomycin compound from step (a) with an excess amount of a diamine compound $H_2N$—R—$NH_2$ thereby covalently to couple the latter as a side chain to the mitomycin-C mitomycin compound to produce a mitomycin derivative, (c) isolating and purifying the product of step (b), (d) reacting the mitomycin derivative obtained in step (c) with a polymer carrier containing at least one amino reactive group that reacts to form a covalent linkage with said mitomycin derivative via the amino terminal group of said side chain, said side chain then forming a spacer unit between the polymer and the mitomycin compound to produce a polymer/drug conjugate, and (e) recovering the polymer/drug conjugate of step (d).

18. A method of preparing a conjugate compound of a polymer carrier molecule in the form of a biologically inert macromolecule and a mitomycin (MMC) drug molecule containing an >NH group in their aziridine ring, wherein the MMC molecules are covalently linked to the polymer carrier molecule through biodegradable spacer groups, said method comprising the steps of coupling said spacer groups in the form of an oligopeptide to a MMC molecule via the aziridine imino groups of the latter, purifying the oligopeptide derivative thus formed, and then coupling the purified oligopeptide derivative to the polymer carrier via reactive groups of the latter and reactive terminal amino groups of the oligopeptide spacers to produce the polymer/drug conjugate, and recovering said conjugate.

19. A method of preparing a polymeric prodrug of mitomycin-C (MMC) wherein the MMC molecule is coupled via a polymeric carrier, said method comprising:

(a) covalently linking the MMC to oligopeptide spacers by reacting the MMC with an N-terminal protected oligopeptide to produce a MMC/oligopeptide derivative;

(b) removing the protective group from the derivative of step (a); and (c) coupling the deprotected derivative of step (b) to activated groups on the polymer carrier.

20. The method as claimed in claim 19, wherein the terminal amino groups of the oligopeptides are protected by Fmoc protective groups and are activated as the pentafluorophenyl ester, and wherein the polymer carrier is poly[N-hydroxyethyl)-L-glutamine] (PHEG) which is coupled via 4-nitrophenyl chloroformate activated groups to reactive terminal amino groups of the deprotected oligopeptide spacers linked to the MMC molecules.

21. The process as claimed in claim 1 wherein the mitomycin-C or mitomycin compound is modified by reacting said mitomycin compound with an activating agent so as to convert the mitomycin aziridine ring >NH group into an activated group which reacts with aliphatic amines, wherein the polymer carrier with which said reactive mitomycin derivative is reacted is a poly(amidoamine) polymer having pendant side chains providing said spacer units, said side chains terminating in a reactive amine group that couples covalently with said activated mitomycin aziridine ring >NH group to form the polymer/drug conjugate.

22. The process as claimed in claim 21 further comprising preliminary step of modifying a poly(amidoamine) polymer having side chains terminating in hydroxyl or carboxyl groups by treating with a carbonyl diimidazole (CDI) or other activating agent and a diamine compound to prepare the said poly(amidoamine) polymer with which said reactive mitomycin derivative is reacted.

23. The polymer/drug conjugate prepared by the process as claimed in claim 1 wherein the polymer carrier is poly [N-(2-hydroxyethyl)-L-glutamine] (PHEG) or a salt thereof coupled to MMC molecules through tripeptide or tetrapeptide spacers which comprising a hydrophobic terminal amino acid and which are degradable in acidic solution by lysosomal enzymes and by the enzyme collagenase IV, said conjugate being less toxic towards bone marrow than MMC.

24. A mitomycin derivative having a side chain terminated with an amino or protected amino group for use as an intermediate compound in synthesising polymer carrier conjugates in accordance with a process as claimed in claims 1, said derivative having a general formula

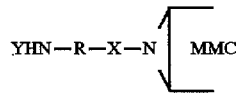

25. A reactive mitomycin derivative, produced by treating a mitomycin compound containing an >NH group in the aziridine ring thereof with carbonyl diimidazole and isolating the product, for use as an intermediate compound in carrying out the process claimed in claim 1.

26. A pharmaceutical formulation containing a polymer carrier and mitomycin-C conjugate compound wherein said conjugate compound is prepared by the process as claimed in claims 1.

* * * * *